(12) United States Patent
Brannan

(10) Patent No.: US 11,071,566 B2
(45) Date of Patent: Jul. 27, 2021

(54) INTRODUCING TROCAR WITH CRYO-FIXATION OF ACCESS CANNULA

(71) Applicant: COVIDIEN LP, Mansfield, MA (US)

(72) Inventor: Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 410 days.

(21) Appl. No.: 15/670,205

(22) Filed: Aug. 7, 2017

(65) Prior Publication Data

US 2018/0055538 A1 Mar. 1, 2018

Related U.S. Application Data

(60) Provisional application No. 62/378,752, filed on Aug. 24, 2016.

(51) Int. Cl.
| | | |
|---|---|---|
| *A61B 17/34* | (2006.01) | |
| *A61B 17/02* | (2006.01) | |
| *A61M 39/02* | (2006.01) | |
| *A61M 39/06* | (2006.01) | |
| *A61B 18/02* | (2006.01) | |

(Continued)

(52) U.S. Cl.
CPC ...... *A61B 17/3423* (2013.01); *A61B 17/0218* (2013.01); *A61B 17/3417* (2013.01); *A61B 17/3462* (2013.01); *A61M 39/02* (2013.01); *A61B 17/3496* (2013.01); *A61B 18/02* (2013.01); *A61B 2017/00092* (2013.01); *A61B 2017/00119* (2013.01); *A61B 2017/3488* (2013.01); *A61B 2018/0212* (2013.01);

(Continued)

(58) Field of Classification Search
CPC .......... A61M 39/02; A61M 2039/0626; A61B 17/3423; A61B 17/3417; A61B 17/0218; A61B 17/3462; A61B 2017/3488; A61B 18/02; A61B 2018/0212; A61B 2017/00092; A61B 2017/00119; A61B 2034/2051; A61B 17/3496
See application file for complete search history.

(56) References Cited

U.S. PATENT DOCUMENTS 4,376,376 A * 3/1983 Gregory ............. A61B 17/3203
606/22
6,319,248 B1 * 11/2001 Nahon ............... A61B 18/0218
604/523

(Continued)

*Primary Examiner* — Richard G Louis
(74) *Attorney, Agent, or Firm* — Carter, DeLuca & Farrell LLP

(57) ABSTRACT

A trocar assembly including an obturator, an access cannula, and a reservoir is provided. The access cannula defines a lumen therethrough configured to selectively receive the obturator. The reservoir is configured to be selectively coupled to the obturator such that the reservoir is in fluid communication with a hollow interior portion of the obturator. An obturator is also provided including an elongate body and a connection point. The elongate body extends between proximal and distal portions and is configured to be received within an access cannula. The elongate body defines a hollow interior portion therein. The connection point is disposed on an exterior portion of the elongate body and is configured to be selectively coupled to a fluid reservoir. Rapid expansion of fluid within the hollow interior portion causes tissue in contact with the access cannula to freeze thereto. A method of performing surgery is also provided.

14 Claims, 14 Drawing Sheets

(51) Int. Cl.
*A61B 17/00* (2006.01)
*A61B 34/20* (2016.01)
(52) U.S. Cl.
CPC .............. *A61B 2034/2051* (2016.02); *A61M 2039/0626* (2013.01)

(56) References Cited

U.S. PATENT DOCUMENTS

| | | | | |
|---|---|---|---|---|
| 6,503,246 | B1* | 1/2003 | Har-Shai | A61B 18/02 606/21 |
| 6,824,385 | B1* | 11/2004 | Bain | A61C 17/0202 433/80 |
| 2002/0010460 | A1* | 1/2002 | Joye | A61B 18/0218 606/21 |
| 2004/0215178 | A1* | 10/2004 | Maurice | A61B 18/02 606/22 |
| 2005/0038422 | A1* | 2/2005 | Maurice | A61B 18/02 606/21 |
| 2007/0088247 | A1* | 4/2007 | Bliweis | A61B 1/00098 604/22 |
| 2007/0219544 | A1* | 9/2007 | Gowda | A61B 18/20 606/16 |
| 2007/0233054 | A1* | 10/2007 | Babaev | A61B 17/22004 606/20 |
| 2012/0095517 | A1* | 4/2012 | Muller | A61M 25/0026 606/86 A |
| 2012/0271292 | A1* | 10/2012 | Duong | A61B 18/02 606/26 |
| 2013/0090639 | A1* | 4/2013 | Atias | A61B 18/02 606/23 |
| 2015/0265257 | A1 | 9/2015 | Costello et al. | |

* cited by examiner

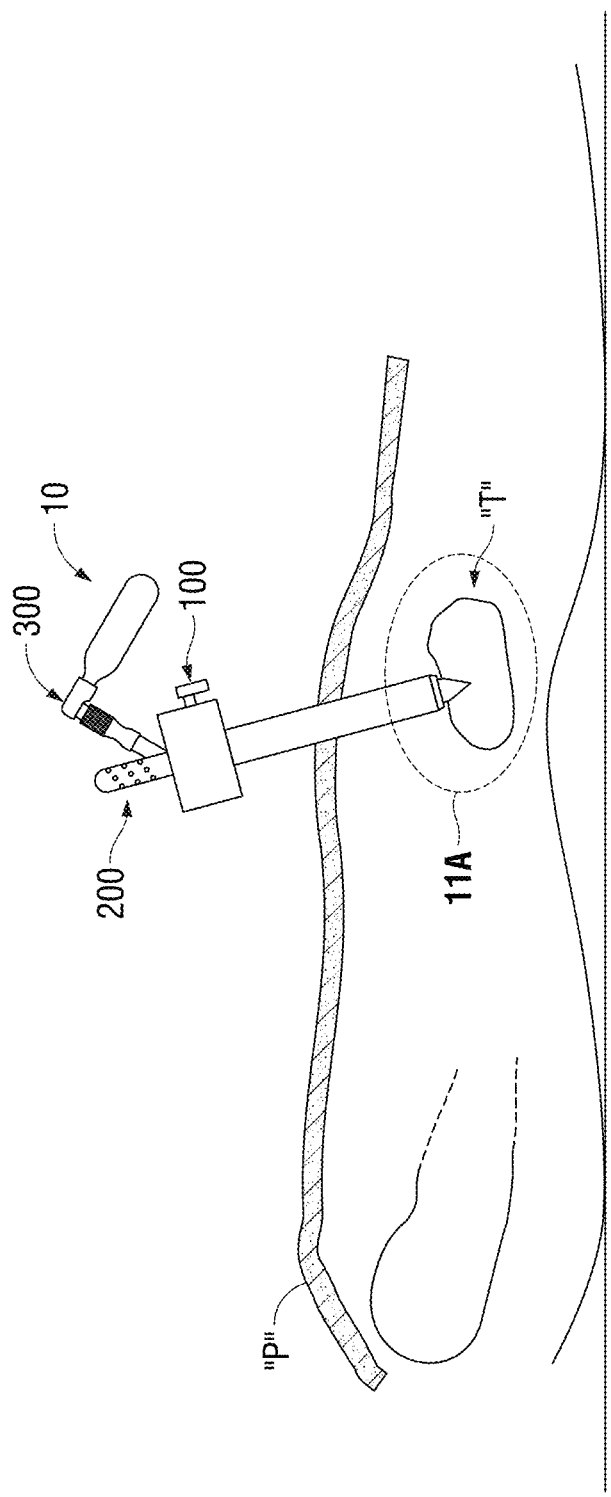

INTRODUCING TROCAR WITH CRYO-FIXATION OF ACCESS CANNULA

CROSS REFERENCE TO RELATED APPLICATION

The present application claims the benefit of and priority to U.S. Provisional Application Ser. No. 62/378,752, filed on Aug. 24, 2016, the entire contents of which are incorporated herein by reference.

BACKGROUND

Technical Field

The present disclosure relates to surgical apparatus, and more particularly, to trocar assemblies and methods for temporarily fixing the location of an access cannula with respect to target tissue.

Description of Related Art

As technology has advanced, surgeons have begun to replace classical open surgical techniques with minimally invasive techniques such as laparoscopic or thoracoscopic surgery in an effort to minimize trauma to surrounding tissue, reduce pain, reduce scarring, and reduce the length of time the patient is required to stay in the hospital. Minimally invasive surgery, such as the laparoscopic approach pioneered in the early $20^{th}$ century, involves the use of small incisions (from one to several), typically no larger than 5-10 mm. Typically, these small incisions are created using a trocar to enable a laparoscope and the surgical tools required to perform the diagnostic or therapeutic procedure to be advanced within the abdominal cavity. A typical trocar assembly may include an obturator (or introducing trocar) and a cannula assembly. The obturator is advanced within the cannula assembly and is used to create a small incision through which the cannula assembly may then be advanced. Once the incision is created, the obturator is removed from the cannula assembly, with the cannula assembly remaining in the incision to provide a conduit in the incision through which the laparoscope or other surgical tools may be advanced.

Often, the distal portion of the trocar assembly (i.e., obturator and cannula assembly) is located adjacent an operative site (i.e., target tissue) such that a surgeon may accurately perform the surgical procedure. However, as the obturator is removed from the cannula assembly and surgical tools are advanced therein, the cannula assembly may shift. This shifting may be caused by patient breathing, patient movement, or the physical manipulation of the cannula assembly, obturator, and/or tools. Any shift in the location of the cannula assembly makes it more difficult for a surgeon to accurately perform the procedure on the target tissue.

One solution to this problem is adhesive needle guides capable of adhering the cannula assembly to the surface of the skin. However, these adhesive needles guides fail to solve the problem of a migrating cannula assembly or even exacerbate the problem due to being adhered to the patient's skin rather than the target tissue. Therefore, the cannula assembly moves with the patient's skin during breathing, patient movement, or even contact with the surrounding skin during the surgical procedure. Additionally, the patient's internal organs may shift during breathing while the skin remains nearly stationary, thus causing the distal end of the cannula assembly to move relative to the target tissue.

Another solution involves the deployment of barbs, tines, or other similar devices from the cannula assembly and into the surrounding tissue. However, the barbs or tines create a risk that surrounding tissue, blood vessels, bile ducts, or nerves may be damaged or that fistulas may be created between neighboring tissue structures. Further, when encountering denser tissues, the barbs or tines may not travel the intended path; rather, the barbs or tines may deflect and embed in unintended tissues.

A further solution involves the use of an expandable balloon disposed on the cannula assembly. Although this solution minimizes collateral damage to non-target tissues, the outer diameter of the access cannula must increase in size to accommodate additional lumens for inflating/deflating the balloon.

SUMMARY

The present disclosure is directed to a trocar assembly including an access cannula, an obturator, and a reservoir. The obturator defines a hollow interior portion and is configured to be selectively received within a lumen defined through the access cannula. The reservoir is configured to be selectively coupled to the obturator such that when the reservoir is coupled to the obturator, the reservoir is in fluid communication with a hollow interior portion of the obturator. The obturator is configured to permit rapid expansion of a fluid released from the reservoir to cause an exterior surface of the obturator to rapidly cool.

In aspects, the obturator may include a connection point configured to selectively couple to the reservoir.

In certain aspects, the obturator may include a transfer tube disposed within the hollow interior portion of the obturator that is coupled to the connection point and is in fluid communication with the reservoir.

In other aspects, the obturator may include a valve assembly disposed therein that is in fluid communication with the transfer tube. The valve assembly may be configured to be selectively actuated by the reservoir wherein when the valve assembly is actuated a fluid stored within the reservoir is transferred to the transfer tube.

In aspects, the valve assembly may be selected from the group consisting of a fixed pin, Schrader valve, a Dunlop valve, and a Presta valve.

In other aspects, the reservoir may include a coupling configured to selectively dispense a fluid deposed within the reservoir.

In certain aspects, the trocar assembly may include a thermocouple disposed on a distal portion of the access cannula.

In other aspects, the trocar assembly may include an indicator coupled to the thermocouple that is configured to provide an alert when a predetermined temperature is measured by the thermocouple.

In a further aspect of the present disclosure, an obturator including an elongate body and a connection point is provided. The elongate body extends between proximal and distal portions and is configured to be received within an access cannula. The elongate body defines a hollow interior portion therein. The connection point is disposed on an exterior portion of the elongate body and is configured to be selectively coupled to a fluid reservoir. Rapid expansion of a fluid within the hollow interior portion causes a rapid decrease in temperature of the obturator such that tissue in contact with the access cannula freezes thereto to fix the location of the obturator in relation to the tissue.

In aspects, the obturator may include a transfer tube disposed within the hollow interior portion of the elongate body that is configured to receive a fluid.

In certain aspects, the obturator may include a valve assembly disposed within the connection point that is in fluid communication with the transfer tube and is configured to be selectively actuated from a first position where fluid is inhibited from passing therethrough to a second position where fluid is permitted to pass therethrough.

In other aspects, a plurality of orifices may be defined through a proximal portion of the elongate body that is in fluid communication with the hollow interior portion such that fluid that has expanded within the hollow interior portion is exhausted to atmosphere through the plurality of orifices.

In aspects, the obturator may include a shield disposed on a wall of the hollow interior portion of the elongate body that is configured to inhibit heat transfer from a fluid to the elongate body.

In other aspects, the shield may be selectively movable to vary the location at which tissue freezes relative to the obturator.

In accordance with yet another aspect of the present disclosure, a method of performing surgery is provided. The method of performing surgery includes advancing an obturator within a lumen defined through an access cannula, penetrating an identified target tissue using a sharp distal end defined on a distal portion of the obturator, advancing the access cannula, with the obturator received therein, within the target tissue, transferring a fluid to a hollow interior portion defined by the obturator, wherein transfer of the fluid to the hollow interior portion cause the fluid to rapidly expand and cool the obturator and access cannula, freezing the target tissue to the cooled access cannula to temporarily adhere the target tissue to the access cannula, removing the obturator from the lumen of the access cannula, and advancing a tool within the lumen of the access cannula to treat the target tissue.

In aspects, transferring the fluid to the hollow interior portion may include coupling a reservoir containing fluid to the obturator.

In certain aspects, the method of performing surgery may include navigating the obturator and access cannula to the target tissue using a navigation system.

In other aspects, navigating the obturator and access cannula to the target tissue may include detecting a sensor disposed on a distal portion of the obturator.

In aspects, the method of performing surgery may include navigating the obturator and access cannula to the target tissue using a bevel defined on a distal portion of the obturator.

In certain aspects, navigating the obturator may include rotating the obturator to orient the bevel such that during an advancement of the obturator within the target tissue the bevel causes the obturator to travel in a particular direction.

BRIEF DESCRIPTION OF THE DRAWINGS

Various aspects and features of the present disclosure are described hereinbelow with references to the drawings, wherein:

FIG. 11 is a side, cross-sectional view of a patient's abdominal cavity including the trocar assembly of FIG. 1 shown as being advanced within target tissue;

DETAILED DESCRIPTION

Figure 1:
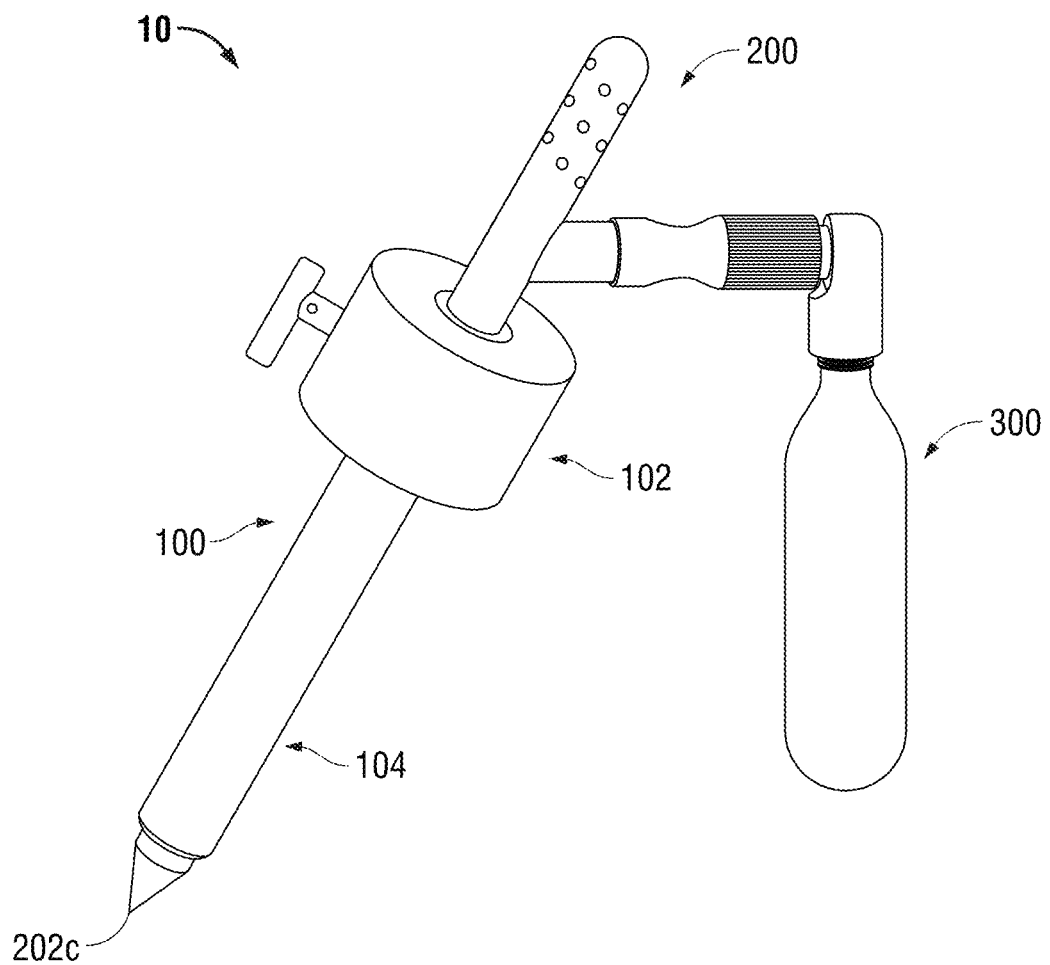
FIG. 1 is a perspective view of a trocar assembly provided in accordance with the present disclosure capable of temporarily fixing an access cannula of the trocar assembly to tissue.
Figure 2:
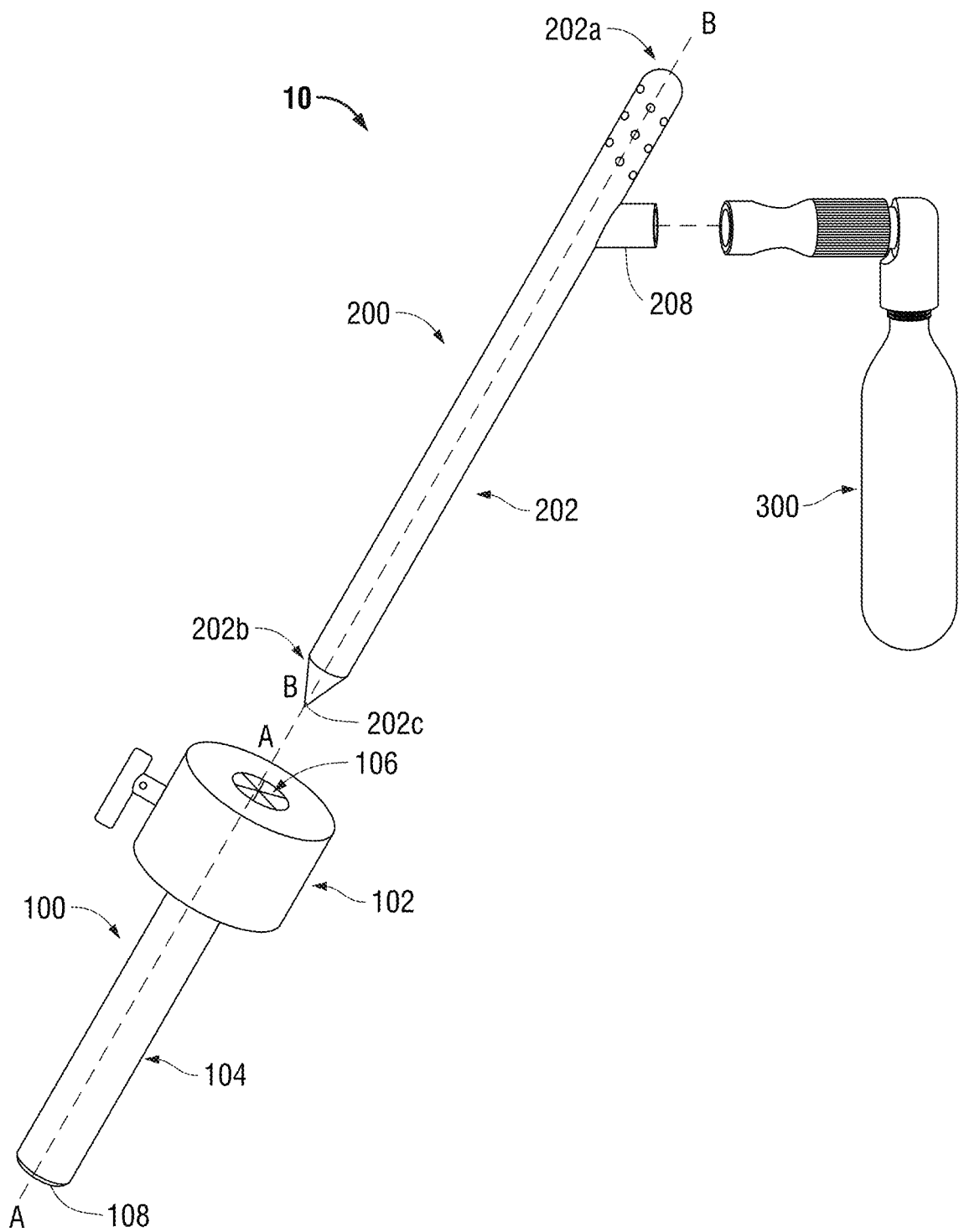
FIG. 2 is a perspective view, with parts separated, of the trocar assembly of FIG. 1.

The present disclosure is directed to trocar assemblies and methods for temporarily fixing the location of an access cannula with respect to target tissue. As described herein, the trocar assemblies and methods include a trocar assembly having an access cannula, an obturator capable of being advanced within the access cannula, and a fluid reservoir. The fluid reservoir is configured to inject a fluid within a chamber defined within an interior portion of the obturator. The rapid expansion of the fluid within the chamber causes the walls of the obturator and adjacent walls of the access cannula to rapidly cool, which in turn, causes the tissue in contact with the access cannula to temporarily freeze and adhere to the walls of the access cannula. By freezing the tissue to the walls of the access cannula, a distal portion of the access cannula is temporarily affixed to the target tissue, inhibiting movement of the distal portion of the access cannula relative to the target tissue. In embodiments, the trocar assemblies described herein may be navigated within a patient to the target tissue through the use of an Electromagnetic Navigation (EMN) System. Further still, the trocar assemblies described herein may utilize a steering mechanism such that the distal portion of the trocar assembly may be more easily navigated to the target tissue. The trocar assemblies and method detailed herein enable clinicians to accurately treat target tissue by minimizing excess access cannula movement relative to the target tissue thereby increasing the accuracy of the treatment, reducing the duration of the procedure, and reducing patient trauma.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Although the trocar assemblies and methods of use detailed herein are generally described with respect to the liver, it is contemplated that the trocar assemblies and methods of use may be applied to any organ or tissue requiring treatment of an interior portion thereof (i.e., the lungs, kidneys, or the like). As can be appreciated, it is envisioned that the trocars detailed herein may be used during laparoscopic or thoracoscopic approaches.

With initial reference to FIGS. 1-8, a trocar assembly capable of being temporarily fixed relative to target tissue is illustrated and generally identified by reference numeral 10. Trocar assembly 10 includes an access cannula 100, an obturator or introducing trocar assembly 200, and a reservoir 300. The access cannula 100 may be any access cannula suitable for use in a minimally invasive surgical procedure. In one non-limiting embodiment, the access cannula 100 includes a cannula housing 102 and a cannula sleeve 104 extending distally from the cannula housing 102 defining a longitudinal axis A-A. It is contemplated that either or both of the cannula housing 102 and the cannula sleeve 104 may be transparent in part or in whole and may be constructed from any suitable biocompatible material. In embodiments, the cannula sleeve 104 may be formed from a resilient material to permit selective manipulation of the curvature of the cannula sleeve 104 off of the longitudinal axis A-A, as will be described in further detail hereinbelow.

The cannula housing 102 and the cannula sleeve 104 define a lumen 106 (FIG. 2) therethrough adapted to receive the obturator 200 or any suitable surgical instrument therein. In embodiments, the access cannula 100 may include an internal seal (not shown) such as a duck-bill valve or other zero closure valve adapted to close in the absence of a surgical instrument or obturator in order to prevent insufflation gases from leaking through the access cannula 100. The distal portion of the cannula sleeve 104 may define a beveled edge 108 (FIG. 2) located at or near the distal end to reduce the insertion force required to advance the cannula sleeve 104 within an incision. It is contemplated that the beveled edge 108 may include any suitable profile capable of facilitating insertion of the cannula sleeve 104 through tissue, such as planar, arcuate, curvilinear, or the like.

The obturator assembly 200 includes an elongate member 202 extending between proximal and distal portions 202a and 202b, respectively, defining a longitudinal axis B-B, and defines a sharp distal end 202c configured to penetrate tissue. The elongate member 202 defines a hollow interior portion or cavity 204 (FIG. 3B) extending from a proximal portion to a distal portion of the elongate member 202 along longitudinal axis B-B. A distal portion of the elongate member 202 defines a connection point 208. The connection point 208 extends from the elongate member 202 and defines an acute angle α with respect to the longitudinal axis B-B, although other configurations are also contemplated. As can be appreciated, the connection point 208 may be integrally formed with the elongate member 202 or may be coupled to the elongate member 202 using any suitable means, such as welding, adhesives, fasteners, or the like. In one non-limiting embodiment, the connection point 208 may be a port defined in the elongate member 202 (i.e., a through hole or other similar feature). In this manner, a valve or other suitable device may threadably engage the connection point 202 to provide a means for coupling a suitable reservoir, as will be described in further detail hereinbelow.

The connection point 208 defines a bore 208a therethrough that is in fluid communication with the interior portion 204 of the elongate body 202. A valve assembly 212 is disposed within the bore 208a and is configured to transfer a fluid (such as a liquid or a gas) from the reservoir 300 and into the interior portion 204 of the elongate member 202. It is contemplated that the valve assembly 212 may be separate from the connection point 212. In this manner, the valve assembly 212 may be selectively coupled to the bore 208a by threadably engaging the valve assembly 212 to the bore 208a. In embodiments the valve assembly 212 may be a one way valve to permit the flow of fluid into the interior portion 204 of the elongate body 202 while inhibiting the flow of fluid back out of the valve assembly 212. It is contemplated that any suitable valve may be utilized, such as a Schrader, a Dunlop, a Presta, a bayonet, or any Compressed Gas Association (CGA) connection suitable for use with the particular fluid stored within the reservoir 300. In embodiments, a proximal portion of the connection point 208 may define exterior threads 208b adapted to threadably engage a coupling of the reservoir 300. In this manner, a clinician does not need to provide pressure on the reservoir 300 to continuously couple the reservoir 300 to the connection point 208. Rather, the clinician may threadably engage the reservoir to the connection point 208, thereby freeing the clinician's hands for other tasks.

It is further envisioned that the valve assembly 212 may be a pin fixedly supported within an interior portion of the connection point 208 (i.e., the pin does not translate or otherwise move relative to the connection point 208). In this manner, the pin is configured to selectively engage a corresponding valve disposed on the reservoir 300 to enable passage of fluid from the reservoir and into the interior portion 204 of the obturator 200, as will be described in further detail hereinbelow. As can be appreciated, the pin may be fixedly supported within the bore 208a using any suitable means capable of enabling fluid to pass around the pin and into the interior portion 204 of the obturator 200.

The connection point 208 is in fluid communication with a transfer tube 210 disposed within the bore 208a that is in fluid communication with the valve assembly 212. In this manner, as the valve assembly 212 is opened, the fluid from within the reservoir 300 is transferred to the transfer tube 201. The transfer tube 210 is sealed to the valve assembly using any suitable means, such as adhesives, welding, mechanical fastening, rubber grommets, or the like. The transfer tube 210 extends from the valve assembly 212 in a distal direction along longitudinal axis B-B within the interior portion 204 of the elongate body 202 and terminates at a distal location therewithin. As can be appreciated, the location at which the transfer tube 210 terminates within the interior portion 204 of the elongate member 202 dictates the location at which the tissue will temporarily freeze to the exterior of the access cannula 100. Accordingly, it is contemplated that the location at which the transfer tube 210 terminates within the interior portion 204 may vary depending on the target tissue and the needs of the procedure being performed (i.e., cause the tissue to freeze at a more proximal portion of the access cannula 100 to limit bleeding, or the like) In one embodiment, the transfer tube 210 may be releasably coupled to the connection point 208 using any suitable means such that the transfer tube 210 may be freely exchanged with transfer tubes of varying lengths. In this manner, a clinician may select a transfer tube 210 having a specific length for the procedure being performed and couple it to the connection point 208. After the procedure is complete, the transfer tube 210 may be removed such that the transfer tube 210 and access cannula 200 may be sterilized. Alternatively, it is envisioned that the length of the transfer tube 210 may be manually adjusted by a clinician using any suitable means, such as a lever, threaded coupling, or the like. In this manner, the transfer tube 210 may be formed from one or more lengths of tube slidably coupled to one another or the transfer tube 210 may be slidably disposed within interior portion 204 of the elongate member 202.

Rather than the transfer tube 210 being adjustable, it is contemplated that the interior portion 204 of the elongate member 202 may include a coating, film, or shield 214 (FIG. 3D) formed from a low thermal conductivity material capable of inhibiting the transfer of heat across specific portions of the elongate member 202. In this manner, the heat transfer between the expanding fluid and the walls of the elongate member 202 can be focused on a specific portion of the elongate member 202 that is uncoated and/or unshielded. In embodiments, the shield 214 may be movable within the interior portion 204 of the elongate body, thereby allowing a clinician to adjust the location at which the access cannula 100 may be temporarily fixed to the target tissue. As can be appreciated, the interior walls of the access cannula 100 may include a similar coating or film to define the location at which the tissue freezes to the access cannula 100.

It is further contemplated that the type of fluid stored within the reservoir 300 can be varied depending upon the needs of the procedure being performed. In particular, in a procedure requiring a large amount of cooling, a liquid may be employed to take advantage of the phase change from liquid to gas (i.e., the heat of vaporization absorbs a greater amount of energy from the surrounding tissue). In contrast, where less cooling is required, the liquid may be a gas. In this manner, it is envisioned that the depth (or amount) of tissue that is frozen may be varied by utilizing various liquids, thereby enabling a clinician to vary the amount of time the access cannula 100 may be adhered to the tissue. As can be appreciated, each of the above described methods of varying the location at which tissue freezes to the access cannula 100 may utilize either a liquid or gas.

Figure 3A:
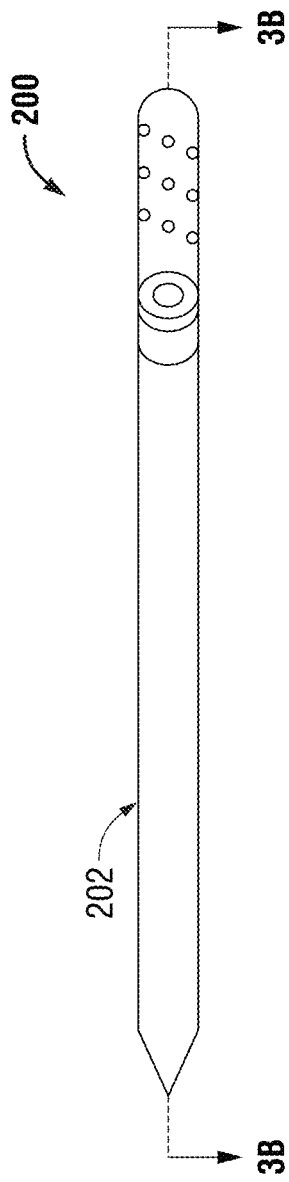
FIG. 3A is a side view of an obturator of the trocar assembly of FIG. 1.
Figure 3B:
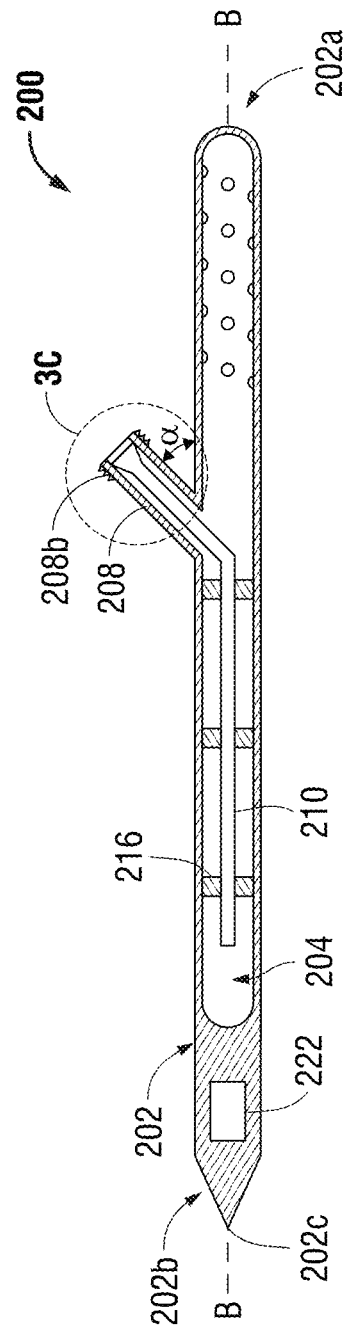
FIG. 3B is a side, cross-sectional, view of the obturator taken along section line 3B-3B of FIG. 3A.
Figure 3C:
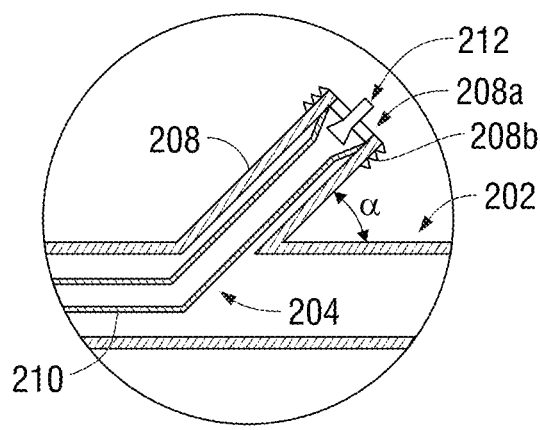
FIG. 3C is an enlarged view of the area of detail indicated in FIG. 3B.
Figure 3D:
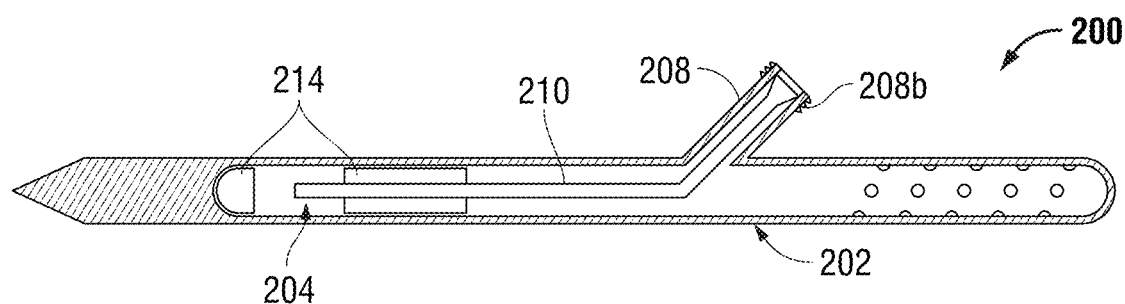
FIG. 3D is a side, cross-sectional view, of an alternate embodiment of an obturator provided in accordance with the present disclosure.
Figure 3E:
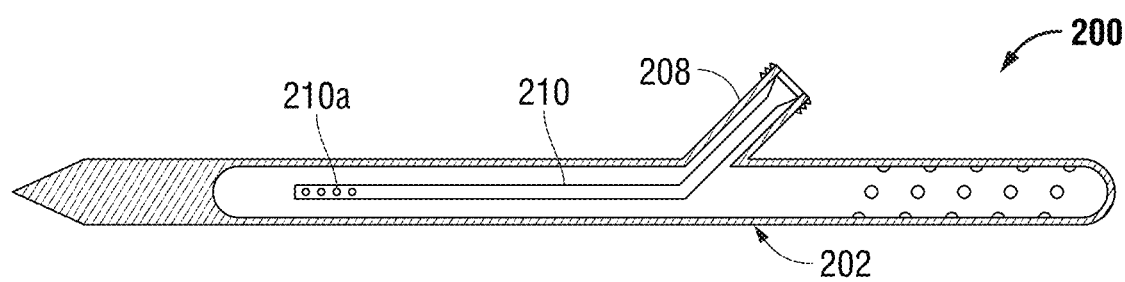
FIG. 3E is a side, cross-sectional view, of yet another embodiment of an obturator provided in accordance with the present disclosure.
Figure 4:
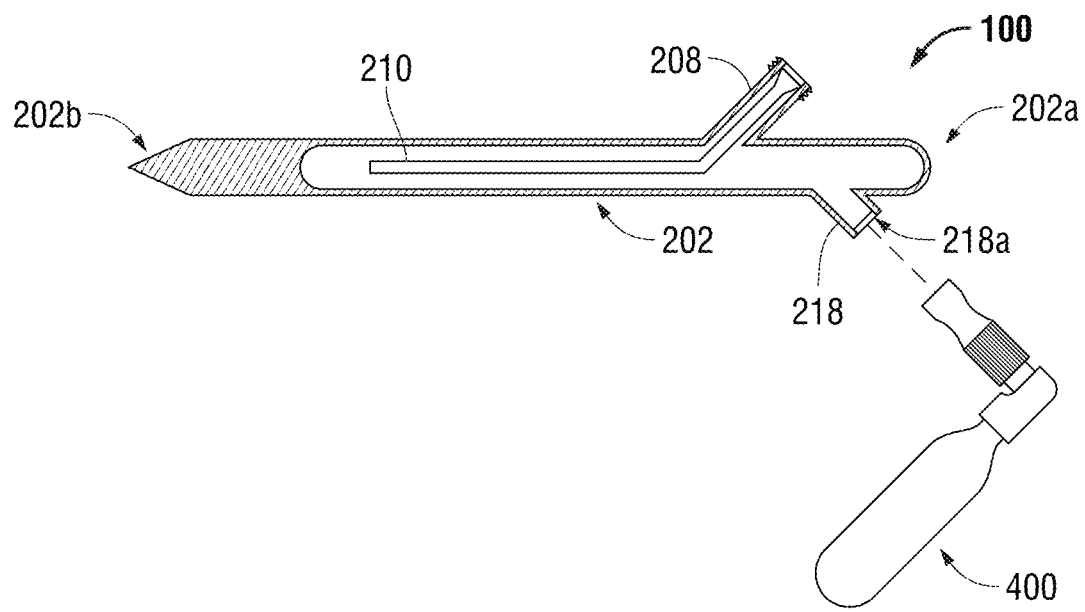
FIG. 4 is a side, cross-sectional view, of still another embodiment of an obturator provided in accordance with the present disclosure.
Figure 5:
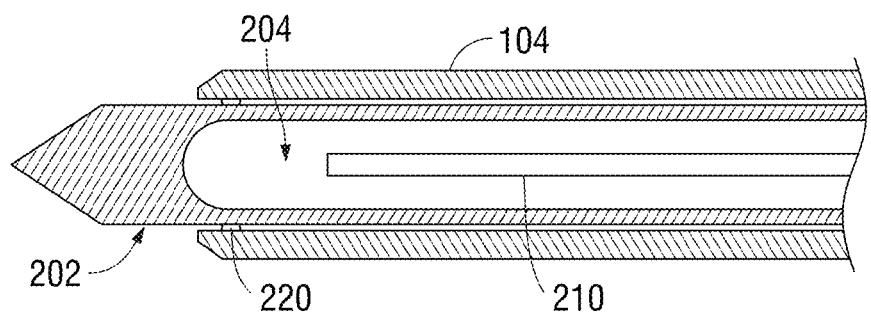
FIG. 5 is an enlarged partial view, which shows a distal portion of the obturator of FIG. 3A.
Figure 6:
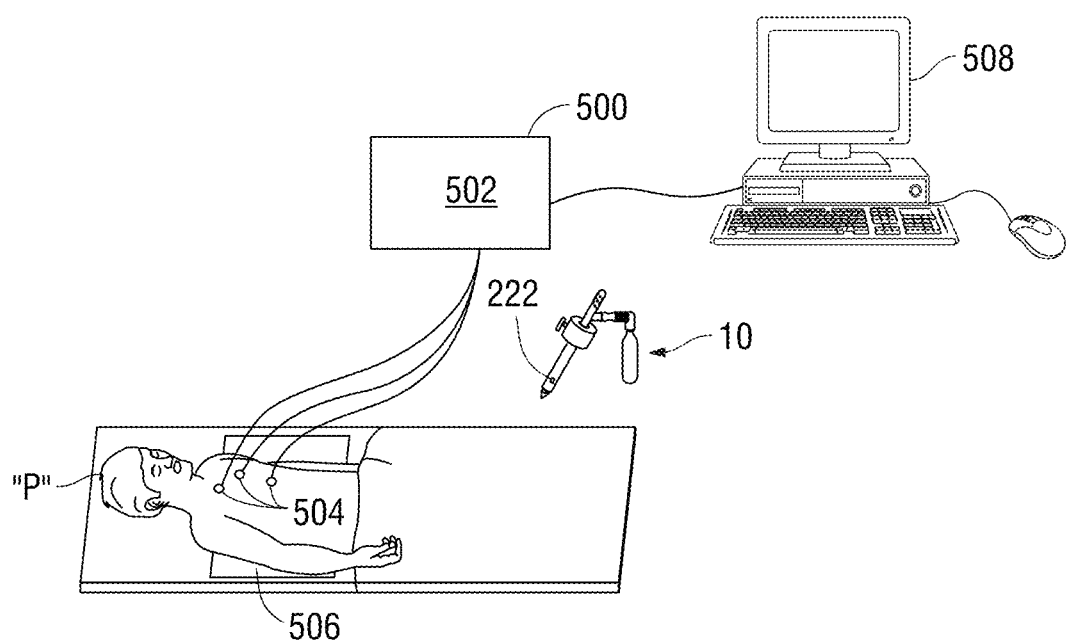
FIG. 6 is a perspective view of a navigation system capable of being used with the trocar assembly of FIG. 1.
Figure 7:
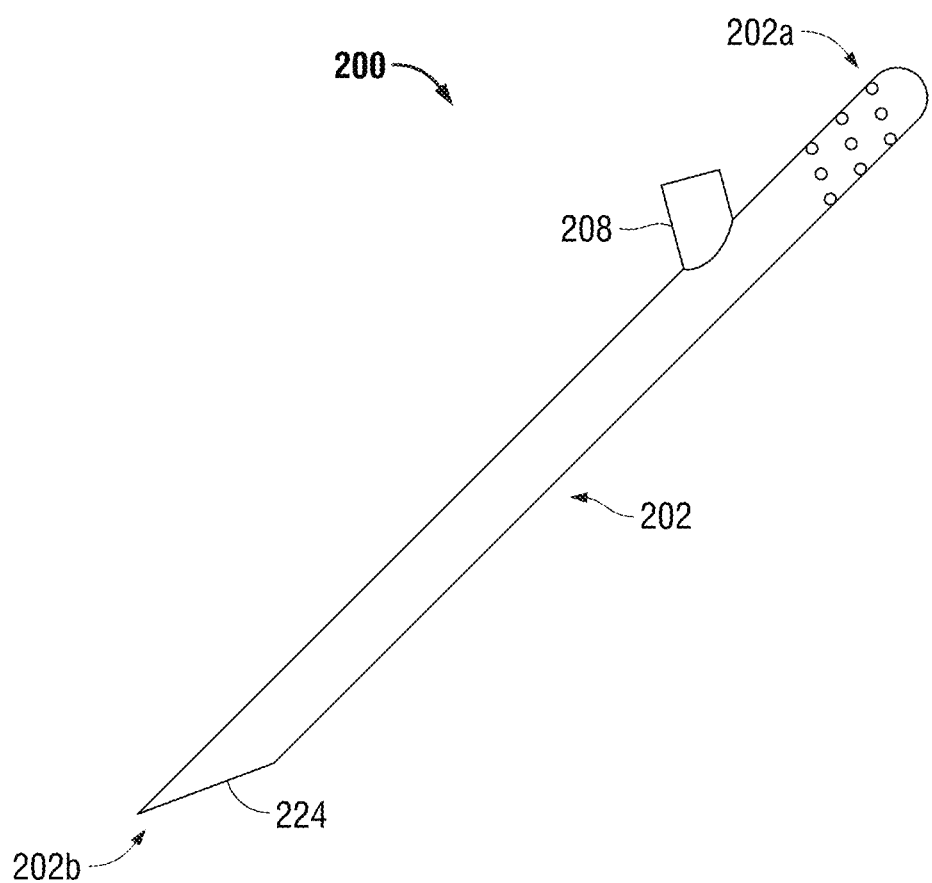
FIG. 7 is a perspective view of yet another embodiment of an obturator provided in accordance with the present disclosure.
Figure 8:
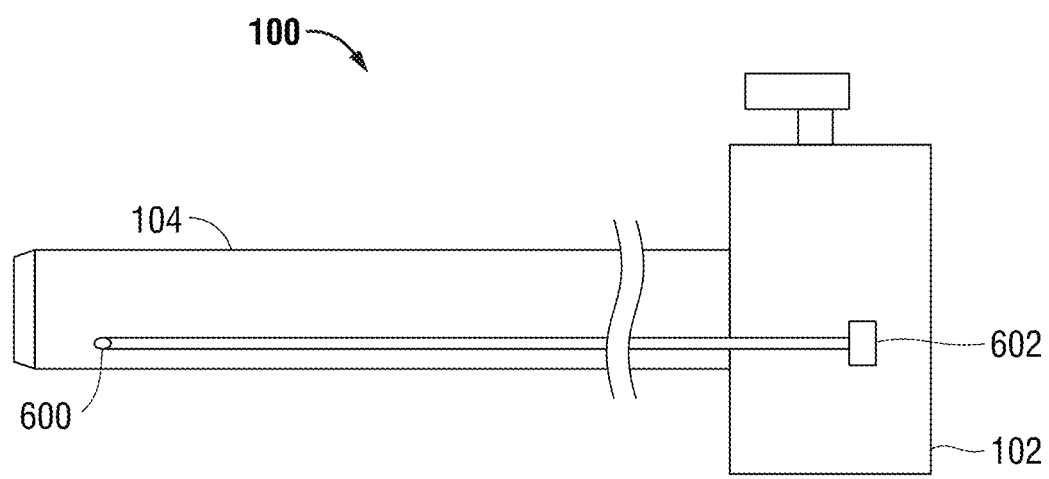
FIG. 8 is a perspective view of a cannula assembly of the trocar assembly of FIG. 1, shown with a thermocouple coupled thereto.

As best illustrated in FIG. 3B, the transfer tube 210 may be supported within the interior portion 204 of the elongate body 202 using one or more spacers 216 disposed within the interior portion 204. The spacers 216 are formed from any suitable material capable of insulating the walls of the elongate body 202 from the transfer tube 210, such as polyethylene, polytetrafluorethylene (PTFE), or other suitable metallic, polymeric, or ceramic materials, although it is contemplated that the spacers 216 may not be formed from a material capable of insulating the walls. Each spacer 216 includes a plurality of cavities or voids (not shown) such that the fluid released within the interior portion 204 of the elongate member 202 can escape from the distal portion of the interior portion 204 and travel proximally along longitudinal axis B-B and be exhausted, as will be described in further detail hereinbelow. As can be appreciated, each spacer 216 may be formed from a material that resists the formation of ice buildup, and therefore closure of the voids within the spacers, to avoid trapping the fluid distal of the spacers 216 and creating a hazardous situation or risk of the access cannula 200 rupturing. In one non-limiting embodiment, the transfer tube 210 is freely supported within the elongate member 202 (i.e., no spacers 216 are used). As an added safeguard against rupture of the elongate member 202, it is envisioned that the obturator 200 may include any suitable pressure relief valve (not shown) suitable for use with the type of fluid stored within the reservoir 300, the temperature of the fluid within the hollow inner portion 204, and calibrated to have a cracking opening or lifting pressure less than the pressure required to rupture the obturator 200. In this manner, the pressure relief valve will relieve the pressure build-up within the hollow interior portion 204, thereby preventing an undesired rupture of the elongate member 202.

Although generally illustrated has being formed from a continuous length of tubing having a distal-most opening, it is contemplated that the transfer tube 210 may terminate in a distal wall and include a plurality of radial orifices 210a (FIG. 3E) defined through a distal portion thereof. In this manner, the location at which the fluid escapes from the transfer 210 may be varied depending on the location of the plurality of radial orifices 210a.

A proximal portion of the elongate member 202 defines a plurality of orifices 206 (FIG. 3B) in fluid communication with the interior portion 204 of the elongate member 202 to permit the expanded fluid to be exhausted from the interior portion 204 to atmosphere. Although generally illustrated as being arranged in a helical configuration, it is contemplated that the plurality of orifices 206 may be defined through the elongate member in any suitable configuration, such as linear, offset, or the like. In some instances, the fluid may not be released into the atmosphere due to concerns with air quality, patient safety, and/or hospital personnel safety within the operating room. Accordingly, it is envisioned that the obturator 200 may not have orifices defined therein, but rather, may include a second nipple 218 (FIG. 4) configured to releasably mate to an exhaust reservoir 400 in a similar manner that reservoir 300 releasably mates to the connection point 208. In one non-limiting embodiment, the exhaust reservoir 400 may be a balloon or other similar device capable of receiving the exhausted fluid. The second nipple 218 defines a bore therein 218a having a valve (not shown) that is in fluid communication with the inner portion 204 of the elongate member 202 such that the second exhaust reservoir 400 may receive the spent fluid released within the inner portion 204 of the elongate member 202.

As can be appreciated, any patient fluids that are trapped between the obturator 200 and the access cannula 100 may freeze during the expansion of fluid and complicate the removal of the obturator 200 from within the access cannula 100. To alleviate this issue, it is envisioned that the obturator 200 may include a gasket 220 (FIG. 5) disposed distal of the location of the location at which fluid expands such that fluids from the patient cannot travel up from the distal opening of the access cannula 100 into the location intended for freezing. Additionally, it is envisioned that the gasket 220 may serve as a wiper as the obturator 200 is advanced within the access cannula 100. In this manner, the gasket 220 pushes or clears material from an internal portion of the access cannula 100 as the obturator 200 is advanced therein, thereby ensuring that no patient fluids or other materials remain within the access cannula and inadvertently freeze the obturator 200 to the access cannula as the fluid expands. As can be appreciated, the gasket 220 may be any suitable material capable of being utilized in a surgical procedure and resist freezing temperatures, such as a polymeric material (e.g., PTFE, PET, FEP, silocones, or the like), welts of hydrophobic material, or the like.

In embodiments, the obturator 200 may be utilized in conjunction with an electromagnetic navigation (EMN) system 500 (FIG. 6) to more accurately navigate the distal portion of the trocar assembly 10 within the patient and reach an area of interest. In this manner, a distal portion of the obturator 200 includes a sensor 222 (FIG. 3B) disposed therein that is electromagnetically sensitive such that the progress of the trocar assembly 10 within the patient may be monitored by the navigation system 500. The sensor 222 allows a clinician to register the position of the obturator 200 to pre or intra-procedural imaging of the patient's anatomy to more clearly identify the position of the obturator 200 within the patient. In one non-limiting embodiment, the navigation system 500 may be a six degrees-of-freedom electromagnetic tracking system utilizing a tracking module 502, a plurality of reference sensors 504 disposed on the patient "P", a transmitter mat 506 disposed underneath the patient "P," and a computer 508 including software and/or hardware used to facilitate pathway planning, identification of tarter tissue, and navigation to the target tissue. With the use of the navigation system 500, the sensor 222 allows monitoring of the position and orientation of the distal portion of the obturator 200, in six degrees of freedom, relative to the reference coordinate system. For a detailed description of the construction of exemplary navigation systems, reference may be made to U.S. Patent Application Publication No. 2015/0265257 to Costello et al. entitled "Systems, and Methods for Navigating a Biopsy Tool to a Target Location and Obtaining a Tissue Sample Using the Same", filed Dec. 9, 2014, the entire contents of which are incorporated by reference herein.

To further increase the ability of a clinician to navigate the trocar assembly 10 within a patient, the access cannula 100 and the obturator 200 may be formed from a resilient material such that the access cannula 100 and/or obturator 200 may be selectively deformed, enabling a clinician to steer the access cannula 100 and/or obturator 200 within the patient. It is contemplated that any suitable steering mechanism (not shown) capable of selectively deforming the access cannula 100 and/or obturator 200 may be employed, such as a plurality of steering wires, hydraulics, or the like. In one non-limiting embodiment, the access cannula 100 and/or obturator 200 may be formed from a shape memory material such as a shape memory alloy or shape memory polymer.

Further still, the distal portion of the obturator 200 may include a bevel or chamfer 224 (FIG. 7) located at or near the distal end such that the bevel 216 causes the obturator 200 to travel in a particular direction as the obturator is advanced within the patient depending on the orientation of the bevel 224. In this manner, a clinician may rotate the obturator 200 to orient the bevel 224 in various orientations as the obturator 200 is advanced within the patient, thereby enabling a clinician to steer or otherwise guide the obturator 200 to the target tissue.

As can be appreciated, it may be beneficial for the clinician to be able to determine when the tissue has frozen and adhered to the target tissue in order to minimize trauma to the region and to minimize waste (i.e., use the minimal amount of fluid required in order to produce the desired effect). In this manner, it is envisioned that a thermocouple 600 (FIG. 8) or other suitable device capable of measuring temperature may be affixed to the access cannula 100 and/or the obturator 200. The thermocouple 600 may be affixed to the access cannula 100 and/or the obturator 200 at a location where the desired tissue freezing occurs. Although generally illustrated as being coupled to an exterior portion of the cannula sleeve 104, it is contemplated that the thermocouple may be embedded within the cannula sleeve 104, coupled to an interior wall of the lumen 106, or may be coupled to the obturator 200 at any suitable location. The thermocouple 600 may be coupled to an indicator 602 or other device (e.g., LED, audible alarm, tactile feedback, or the like) configured to alert the clinician that the tissue has reached a temperature at which it freezes. It is contemplated that the indicator 602 may be calibrated to the specific tissue being targeted in order to further maximize efficiency of the trocar assembly 10.

Figure 9:
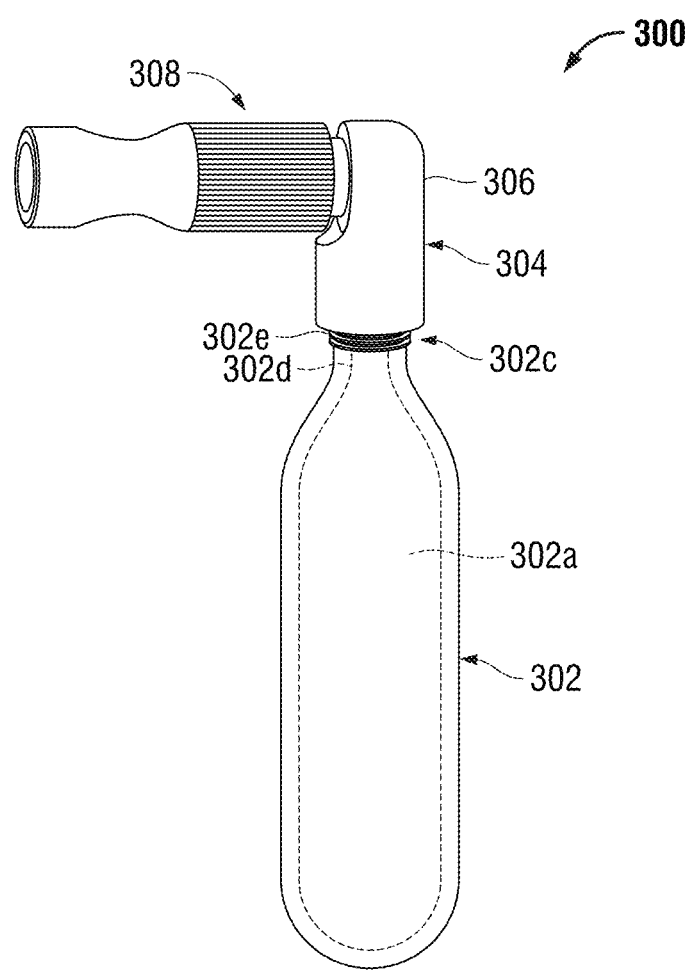
FIG. 9 is a perspective view of a reservoir of the trocar assembly of FIG. 1.
Figure 10:
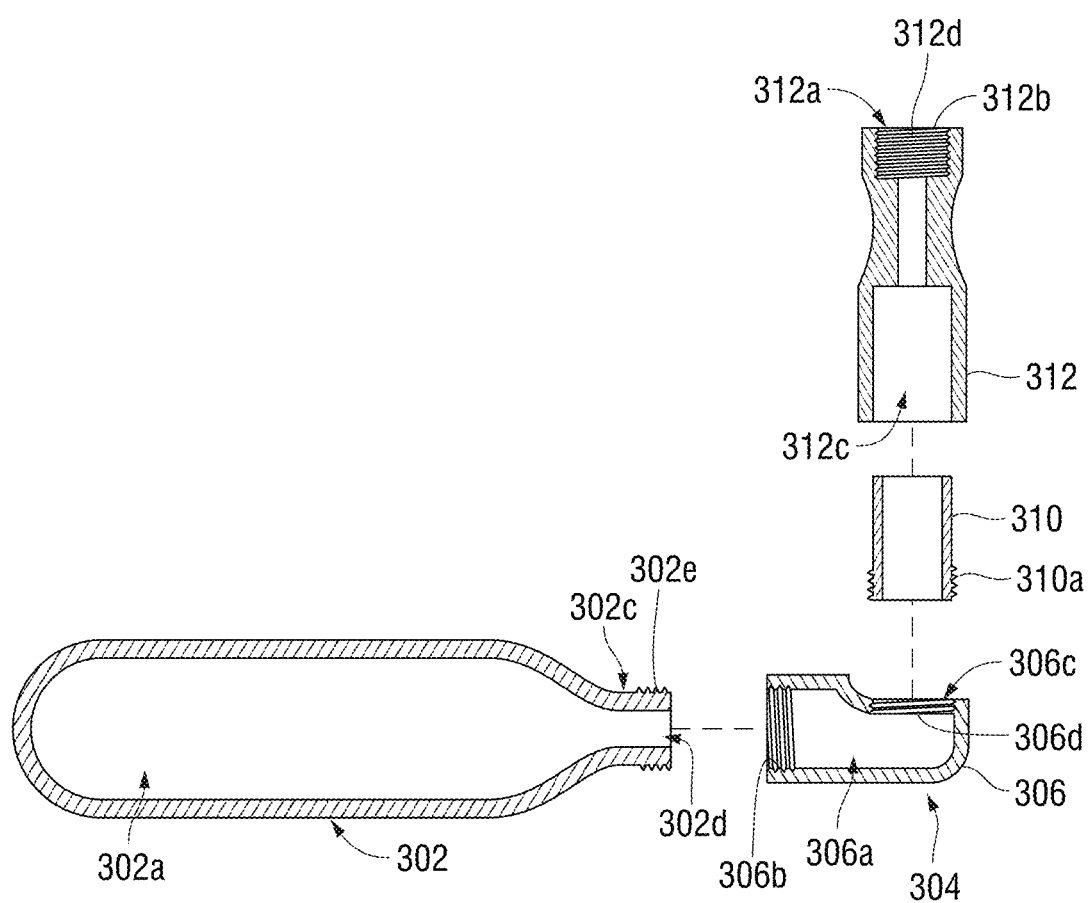
FIG. 10 is a side, cross-sectional view, of the reservoir of FIG. 9, shown with parts separated.

With reference to FIGS. 9 and 10, the reservoir 300 includes a cartridge 302 and a coupling 304. The cartridge 302 includes a generally elongate body defining a hollow interior 302a therein. A proximal portion of the cartridge 302 defines a threaded neck 302c defining an interior bore 302d in fluid communication with the hollow interior portion 302a. The threaded neck 302c defines exterior threads 302e configured to threadably engage corresponding threads of the coupling 304, as will be described in further detail herein. In embodiments, the cartridge 302 may have an unthreaded neck configured to releasably couple to the coupling 304. It is contemplated that the cartridge 302 may be any suitable fluid cartridge known in the art, such as 8 g cartridges, 16 g cartridges, 25 g cartridges, and 38 g cartridges, depending on the needs of the procedure being performed. Although generally storing carbon dioxide $CO_2$, it is contemplated that the reservoir 300 may store any suitable fluid depending on the needs of the procedure being performed.

The coupling 304 includes a threaded coupling 306 and a receiver 308. The threaded coupling 306 includes an elongate body defining an interior cavity 306a therein. A distal portion of the interior cavity 306a defines interior threads 306b configured to threadably engage the exterior threads 302e of the cartridge 302. In embodiments, the interior cavity 306a may selectively couple to a cartridge 302 having an unthreaded neck using any suitable means, such as compression fit or the like. A proximal portion of the elongate body defines a radial bore 306c that penetrates the interior cavity 306a such that the radial bore 306c and the interior cavity 306a are in fluid communication. The radial bore 306c defines interior threads 306d that are configured to threadably engage a portion of the receiver 308, as will be described in further detail hereinbelow.

The receiver 308 includes a guide sleeve 310 and a connector 312 slidably and rotatably disposed thereon. The guide sleeve 310 defines a plurality of threads 310a that are configured to threadably engage the interior threads 306e of the threaded coupling 306 on a first end and slidably receives the connector 312 on a second end. The connector 312 is retained on the guide sleeve 310 using any suitable means, such as a circlip, swage, of the like (not shown). A biasing element (not shown) is interposed between the guide sleeve 310 and the connector 312 such that the connector 312 is biased away from the guide sleeve 310. In this manner, the circlip or other suitable retention means prevents the connector 312 from becoming disengaged from the guide sleeve 310 while maintaining a bias from the biasing element.

The connector 312 includes a first internal bore 312a defining interior threads 312b configured to threadably engage the connection point 208 of the obturator 200, although it is contemplated that the first internal bore 312a may be unthreaded. A second, opposite end of the connector 312 defines a second internal bore 312c that is configured to receive a portion of the guide sleeve therein. A concentrically disposed pin 312d is fixedly retained within the first internal bore 312a using any suitable means and is configured to engage the valve assembly 212 of the obturator 200. In this manner, the pin 312d depresses the valve assembly 212 as the connector 312 is coupled to the connection point 208. A gasket (not shown) or other suitable device is disposed within the internal bore 312a such that when the connector 312 is fully advanced over the connection point 208, the gasket seals against a proximal face of the connection point 208 to inhibit fluid from escaping from the interface between the connector 312 and the connection point 208. In embodiments, the connector 312 includes a valve (not shown) or other similar device that prohibits the fluid from escaping from the cartridge 302 unless the valve is depressed. In this manner, a clinician is required to pull the connector 312 back (i.e., towards the cartridge) against a bias such that the valve is depressed and fluid is permitted to flow from the cartridge 302 and into the obturator 200. As can be appreciated, the connector 312 may be longitudinally fixed (i.e., only permitted to rotate about the guide sleeve 310). In this manner, a clinician rotates the connector 312 about the guide sleeve 310 until the connector 312 is fully threaded onto the connection point 208 and the valve assembly 212 is actuated. A clinician may control the flow of fluid from the reservoir 300 into the obturator 200 by threading and unthreading the connector 312 from the connection point 208 to actuate/close the valve assembly 212. As can be appreciated, any coupling suitable for use with $CO_2$ cartridges and capable of selectively coupling to a valve assembly such as those described hereinabove may be utilized. Examples of reservoirs and couplings described above are manufactured by Lezyne, Genuine Innovations, Spin Doctor, Topeak, and SKS.

In use, with reference to FIGS. 11-14, the obturator 200 is initially advanced within the lumen 106 of the access cannula 100. The obturator 200 continues to be advanced until the obturator 200 is fully advanced within the access cannula 100 and the sharp distal portion 202c of the obturator 200 protrudes from the distal portion of the access cannula 100. The skin of the patient is then penetrated by the sharp distal portion 202c of the obturator 200 and the trocar assembly 10 is advanced within a body cavity of the patient. Next, the sharp distal portion 202c of the obturator is navigated to the target tissue "T". In this manner, the obturator 200 may merely be advanced in a linear fashion, may be tracked using navigation system 500, may be navigated using the bevel 224 of the obturator, or may utilize a shape memory material to navigate the obturator 200 be navigated by means of a shape memory material to the target tissue.

Figure 11A:
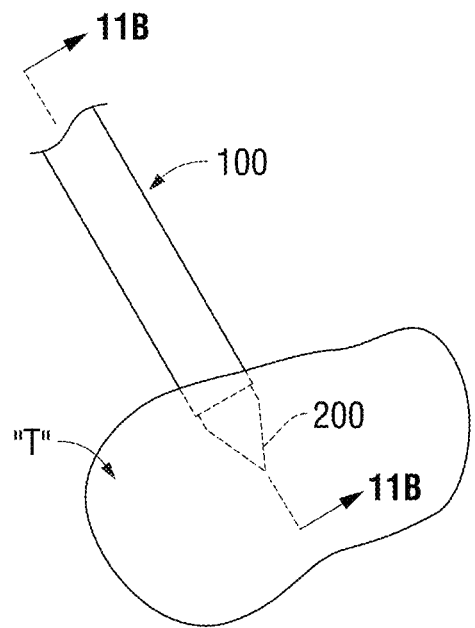
FIG. 11A is an enlarged view of the area of detail indicated in FIG. 11.
Figure 11B:
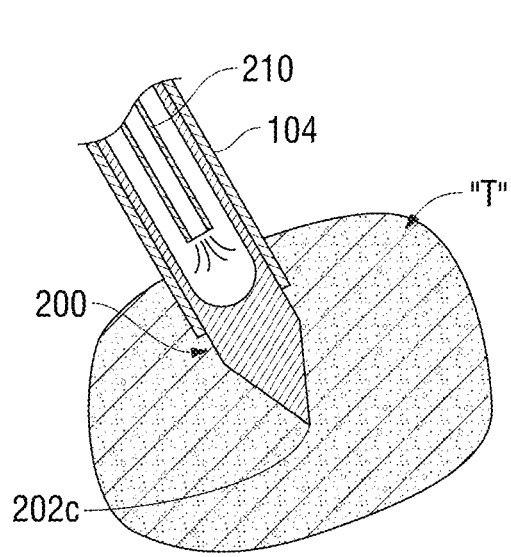
FIG. 11B is a cross-sectional view taken along section line 11B-11B of FIG. 11A.
Figure 11C:
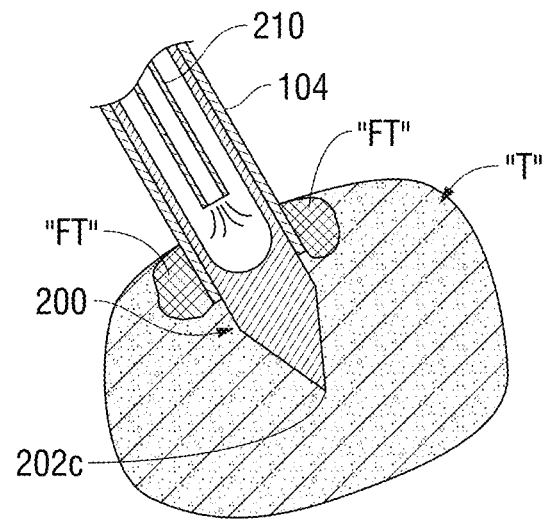
FIG. 11C is a cross-sectional view of the trocar assembly of FIG. 1 showing an access cannula of the trocar assembly adhered to the target tissue.

The sharp distal portion 202c of the obturator is further advanced such that the distal tip 202b of the obturator penetrates the target tissue "T", i.e., the liver, and is continued to be advanced until the distal end of the cannula sleeve 104 of the access cannula 100 is adjacent to the target tissue "T" (FIGS. 11A and 11B). Once the trocar assembly 10 is placed in the intended position, a clinician couples the reservoir 300 to the connection point 208 by rotating the connector 312 of the reservoir 300 in a first direction to threadably engage the connector 312 to the threads 208b of the connection point 208. Alternatively, the receiver 308 of the reservoir 300 may be advanced over the connection point 208 to couple the reservoir 300 to the connection point 208, regardless of whether the connection point 208 is threaded or not. The connector 312 is further rotated in the first direction until the connector 312 is fully seated on the connection point 208. Once the clinician ensures that the distal end of the cannula sleeve 104 is positioned correctly, the clinician pulls the connector 312 away from the obturator 200 to open the valve assembly 212 of the obturator thereby permitting fluid to transfer from the reservoir 300 and into the transfer tube 210 (FIG. 11C). Alternatively, it is contemplated that the reservoir 300 may be coupled to the obturator 200 before the trocar assembly 10 is advanced within the patient.

Figure 12:
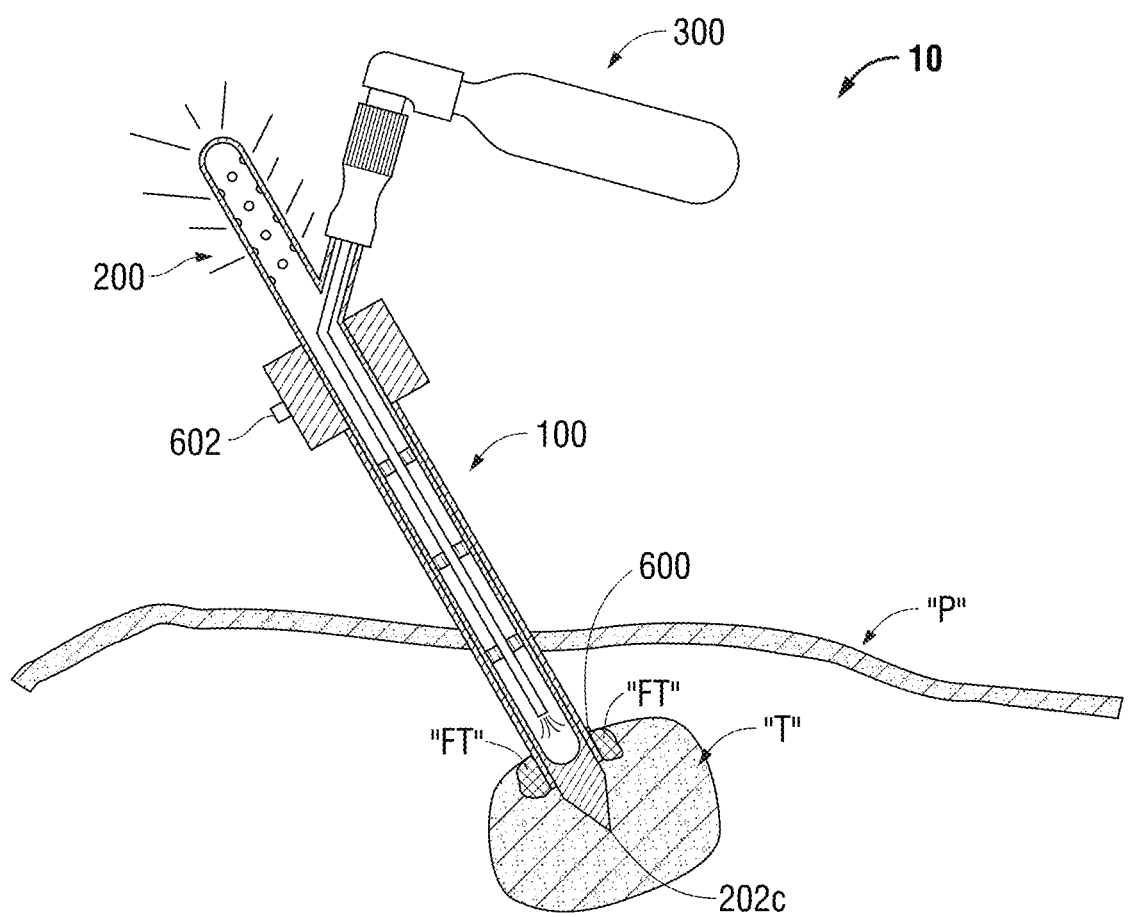
FIG. 12 is a side, cross-sectional view, of a patient showing the trocar assembly of FIG. 1 adhered to tissue of the patient.
Figure 13:
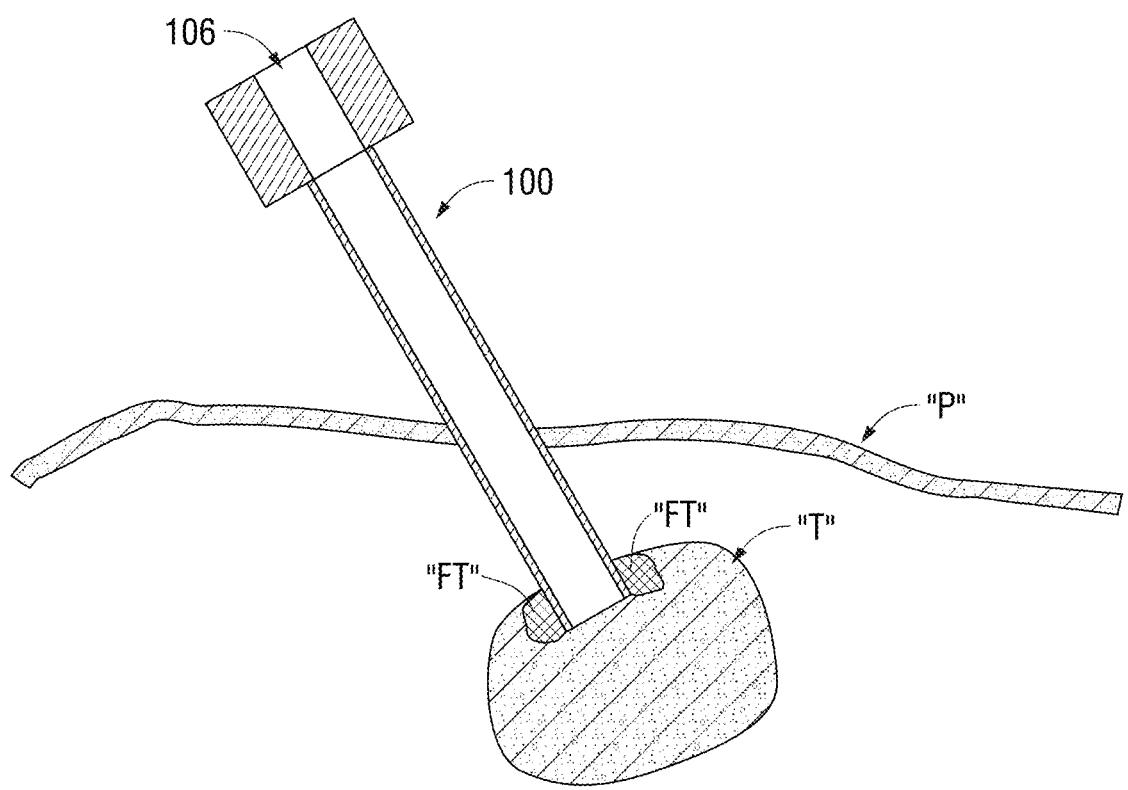
FIG. 13 is a side, cross-sectional view, of a patient showing the obturator removed from the trocar assembly of FIG. 1.
Figure 14:
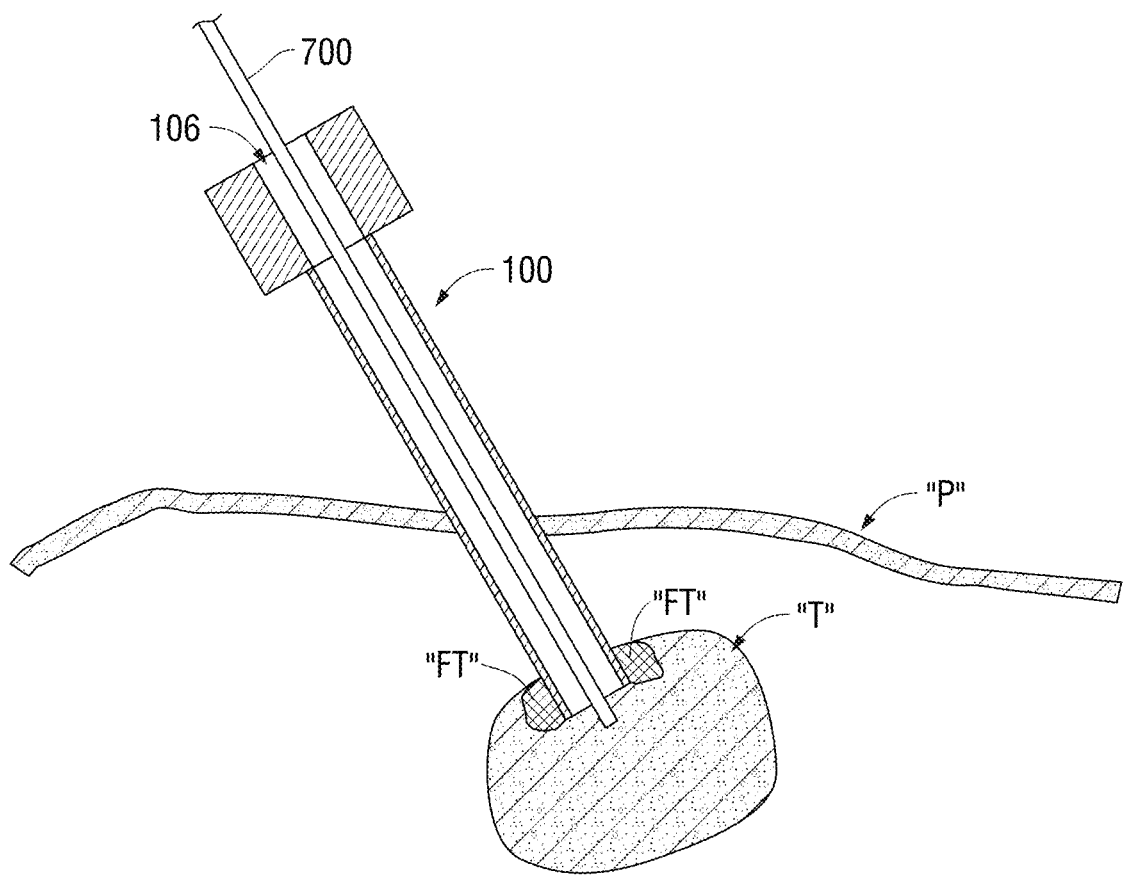
FIG. 14 is a side, cross-sectional view, of a patient showing a surgical tool advanced within the trocar assembly of FIG. 1 and into target tissue.

At this point, the fluid exits the transfer tube 210 and rapidly expands within the interior portion 204 of the elongate member 202 (FIG. 12). The rapid expansion of the fluid within the interior portion 204 causes the temperature of the fluid to rapidly decrease, absorbing the heat from the walls of the elongate member 202 and the access cannula 100. The rapid decrease in temperature of the access cannula 100 causes the tissue in contact with an exterior portion of the access cannula 100 to freeze and cause a frozen tissue zone "FT" surrounding the access cannula 100 thereby temporarily adhering the tissue to the access cannula 100 and temporarily fixing the location of the distal end of the access cannula 100 within the target tissue "T". Depending on the type of tissue being frozen (i.e., density of the tissue, amount of water, etc.), varying amounts of fluid may be required in order to fully adhere the tissue to the access cannula 100. In embodiments, when the walls of the access cannula 100 reach a predetermined temperature (as measured by the thermocouple 600, the indicator 602 will alert the clinician that the tissue has reached a temperature at which it freezes. At this point, the clinician will release the connector 312 to close the valve assembly 212 and terminate the flow of fluid within the transfer tube 210. The reservoir 300 may then be removed from the obturator 200 by rotating the connector 312 in a second, opposite direction and discarded, or if a reusable reservoir 300 has been used, the coupling 304 may be removed from the cartridge 302 and each may be placed in a sterilization chamber and thereafter, the cartridge 302 may be recharged to be used during a future procedure. Once the reservoir 300 has been removed from the obturator 200, the obturator 200 is removed from the access cannula 100 and placed in a sterilization chamber (FIG. 13). In embodiments, the obturator 200 may be removed from the access cannula 100 with the reservoir 300 still coupled thereto. Once the obturator 200 has been fully removed from the access cannula 100, the reservoir 300 may be removed in a similar manner to that described above. With the obturator 200 fully removed from the access cannula 100, a surgical tool 700 or other device (i.e., clip applier, ablation probe, forceps, or the like) may be advanced within the lumen 106 of the access cannula 100 to treat the target tissue (FIG. 14).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A trocar assembly, comprising:
   an access cannula defining a lumen therethrough;
   an obturator defining a longitudinal axis and a hollow interior portion, the obturator configured to be selectively received within the lumen of the access cannula to penetrate target tissue within a patient, the obturator having a fluid port defining an internal bore therethrough in fluid communication with the hollow interior portion and extending from an exterior surface of the obturator at an angle relative to the longitudinal axis defined by the obturator and a plurality of orifices defined through the exterior surface of the obturator proximal to the fluid port and in fluid communication with the hollow interior portion, the plurality of orifices being located outside the patient during use of the obturator to penetrate the target tissue;
   a reservoir that connects to the obturator to place the reservoir in fluid communication with the hollow interior portion defined by the obturator;
   a coupling configured to connect the obturator to the reservoir, the coupling including a first connector that connects to the fluid port and a second connector that connects to the reservoir, wherein fluid released from the reservoir into the hollow interior portion upon connection of the reservoir to the obturator rapidly expands within the hollow interior portion to rapidly cool an exterior surface of the obturator and an exterior surface of the access cannula, thereby freezing the target tissue in contact with the exterior surface of the access cannula to temporarily adhere the frozen target tissue to the exterior surface of the access cannula; and
   a transfer tube disposed within the hollow interior portion and having a distal portion extending along the longitudinal axis defined by the obturator and a proximal portion extending along a longitudinal axis defined by the fluid port, the transfer tube having a distal end disposed at a distal end portion of the hollow interior portion and a proximal end disposed within the internal bore defined through the fluid port such that the reservoir, upon connection to the obturator via the coupling, is in direct fluid communication with the distal end portion of the hollow interior portion via the transfer tube.

2. The trocar assembly according to claim 1, wherein the obturator further includes a valve assembly disposed within the internal bore defined through the fluid port and in fluid communication with the transfer tube, the valve assembly configured to be selectively actuated by the first connector, wherein when the valve assembly is actuated a fluid stored within the reservoir is transferred to the transfer tube via the coupling.

3. The trocar assembly according to claim 2, wherein the valve assembly is selected from the group consisting of a fixed pin, Schrader valve, a Dunlop valve, and a Presta valve.

4. The trocar assembly according to claim 1, further including a thermocouple disposed on a distal portion of the access cannula.

5. The trocar assembly according to claim 4, further including an indicator coupled to the thermocouple, wherein the indicator is configured to provide an alert when a predetermined temperature is measured by the thermocouple.

6. An obturator, comprising:
   an elongate body extending between proximal and distal portions, the elongate body configured to be received within an access cannula and defining a hollow interior portion therein;
   a plurality of orifices formed through an exterior surface of a proximal end portion of the elongate body and disposed in fluid communication with the hollow interior portion defined by the elongate body;
   a fluid port defined by the exterior surface of the elongate body distal to the plurality of orifices, the fluid port configured to connect to a fluid reservoir to fluidly couple the fluid reservoir to the hollow interior portion, wherein a rapid expansion of fluid received within the hollow interior portion from the fluid reservoir upon connection of the fluid port to the fluid reservoir causes a rapid decrease in temperature of the exterior surface of the elongate body and an exterior surface of the access cannula such that tissue in contact with the access cannula freezes and temporarily adheres to the exterior surface of the access cannula to fix the location of the elongate body in relation to the tissue and the expanded fluid is exhausted from the hollow interior portion to atmosphere through the plurality of orifices; and
   a transfer tube disposed within the hollow interior portion and having a distal portion extending along a longitudinal axis defined by the elongate body and a proximal portion extending along a longitudinal axis defined by the fluid port, the transfer tube having a distal end disposed at a distal end portion of the hollow interior portion and a proximal end disposed within an internal bore defined through the fluid port such that the distal end portion of the hollow interior portion is in direct fluid communication with the fluid reservoir upon connection of the fluid port to the fluid reservoir.

7. The obturator according to claim 6, further including a valve assembly disposed within the internal bore defined through the fluid port, the valve assembly being in fluid communication with the transfer tube and configured to be selectively actuated from a first position where fluid is inhibited from passing therethrough to a second position where fluid is permitted to pass therethrough.

8. The obturator according to claim 6, further including a shield disposed on a wall of the hollow interior portion of the elongate body, the shield configured to inhibit heat transfer from the fluid to the exterior surface of the elongate body.

9. The obturator according to claim 8, wherein the shield is selectively movable to vary the location at which tissue freezes relative to the exterior surface of the obturator.

10. The trocar assembly according to claim 1, wherein the expanded fluid is exhausted from the hollow interior portion to atmosphere through the plurality of orifices.

11. The trocar assembly according to claim 1, wherein the fluid port extends from the exterior surface of the obturator at an acute angle relative to a longitudinal axis defined by the obturator.

12. The trocar assembly according to claim 1, further comprising an electromagnetic sensor disposed on the obturator and configured to communicate with a navigation system to register a position of the obturator within a patient to an image of the patient.

13. A trocar assembly, comprising:
- an obturator defining a fluid cavity and configured to be selectively received through an access cannula to penetrate target tissue within a patient;
- a plurality of orifices defined through an exterior surface of the obturator, the plurality of orifices being located outside the patient during use of the obturator to penetrate the target tissue;
- a fluid port defining an internal bore in fluid communication with the fluid cavity and extending from an exterior surface of the obturator distal to the plurality of orifices and at an angle relative to a longitudinal axis defined by the obturator;
- a coupling having a first connector that connects to the fluid port of the obturator and a second connector that connects to a fluid reservoir, wherein connection of the fluid reservoir to the obturator via the coupling causes fluid from the fluid reservoir to be received within the fluid cavity to cool an exterior surface of the obturator; and
- a transfer tube disposed within the fluid cavity and having a distal portion extending along the longitudinal axis defined by the obturator and a proximal portion extending along a longitudinal axis defined by the fluid port, the transfer tube having a distal end disposed at a distal end portion of the fluid cavity and a proximal end disposed within the internal bore such that the distal end portion of the fluid cavity is in direct fluid communication with the fluid reservoir upon connection of the fluid reservoir to the obturator via the coupling.

14. The trocar assembly according to claim 13, wherein the fluid port extends from the exterior surface of the obturator at an acute angle relative to the longitudinal axis defined by the obturator.

* * * * *